(12) United States Patent
Foster et al.

(10) Patent No.: US 11,278,304 B2
(45) Date of Patent: Mar. 22, 2022

(54) INTRODUCER WITH TISSUE POCKET OPTIMIZER (71) Applicant: Cardiac Pacemakers, Inc., St. Paul, MN (US)

(72) Inventors: Arthur J. Foster, Blaine, MN (US); Jean M. Bobgan, Maple Grove, MN (US); David P. Stieper, North Branch, MN (US); JoAnna Trapp Simpson, Eagan, MN (US); Bruce K. Gilbertson, Coon Rapids, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 371 days.

(21) Appl. No.: 15/242,521

(22) Filed: Aug. 20, 2016

(65) Prior Publication Data
US 2017/0049467 A1 Feb. 23, 2017

Related U.S. Application Data (60) Provisional application No. 62/207,912, filed on Aug. 21, 2015.

(51) Int. Cl.
*A61B 17/32* (2006.01)
*A61N 1/05* (2006.01)
(Continued)

(52) U.S. Cl.
CPC .......... *A61B 17/32* (2013.01); *A61B 17/3468* (2013.01); *A61M 37/0069* (2013.01);
(Continued)

(58) Field of Classification Search
CPC ... A61M 37/0069; A61B 2017/320044; A61B 17/3468; A61B 17/32; A61B 2017/347;
(Continued)

(56) References Cited

U.S. PATENT DOCUMENTS 4,592,341 A * 6/1986 Omagari .................... A61F 2/94
600/104
5,505,686 A * 4/1996 Willis ................ A61B 1/00087
600/104
(Continued)

FOREIGN PATENT DOCUMENTS

CN 1827056 A 9/2006
CN 201005759 Y 1/2008
(Continued)

OTHER PUBLICATIONS

International Search Report and Written Opinion issued in PCT/US2016/047933, dated Oct. 12, 2016, 10 pages.

*Primary Examiner* — Kathleen S Holwerda
(74) *Attorney, Agent, or Firm* — Faegre Drinker Biddle & Reath LLP (57) ABSTRACT Various aspects of the present disclosure are directed toward apparatuses, systems, and methods that include a housing having a proximal portion including a proximal opening, distal portion including a distal opening, and an intermediate portion sized to contain a medical device; and an inserter having at least a portion comprising a greater width than at least one other portion of the inserter.

18 Claims, 11 Drawing Sheets (51) Int. Cl.
  *A61N 1/372* (2006.01)
  *A61B 17/34* (2006.01)
  *A61M 37/00* (2006.01)
  *A61N 5/10* (2006.01)

(52) U.S. Cl.
  CPC ........... *A61N 1/0504* (2013.01); *A61N 1/372* (2013.01); *A61B 2017/320044* (2013.01); *A61B 2017/347* (2013.01); *A61N 5/1027* (2013.01); *A61N 2005/1011* (2013.01)

(58) Field of Classification Search
  CPC .............. A61B 1/32; A61B 2017/3456; A61N 1/0504; A61N 1/372; A61N 5/1072; A61N 5/1027; A61N 2005/1011
  USPC .................. 606/108, 129, 190, 200; 623/6.12
  See application file for complete search history.

(56) References Cited

U.S. PATENT DOCUMENTS

| | | | | |
|---|---|---|---|---|
| 5,893,837 | A * | 4/1999 | Eagles | A61F 9/00781 604/264 |
| 7,713,281 | B2 * | 5/2010 | Leeflang | A61B 17/3439 606/194 |
| 8,961,532 | B2 * | 2/2015 | Tremulis | A61M 25/0068 606/108 |
| 2003/0220547 | A1 * | 11/2003 | Holland | A61B 17/00008 600/245 |
| 2004/0144395 | A1 | 7/2004 | Evans et al. | |
| 2005/0090852 | A1 | 4/2005 | Layne et al. | |
| 2005/0149104 | A1 * | 7/2005 | Leeflang | A61B 17/3439 606/198 |
| 2007/0010738 | A1 | 1/2007 | Mark et al. | |
| 2007/0219466 | A1 * | 9/2007 | Tremulis | A61M 25/0068 600/585 |
| 2009/0036917 | A1 | 2/2009 | Anderson | |
| 2010/0063345 | A1 | 3/2010 | Yuasa | |
| 2010/0094252 | A1 | 4/2010 | Wengreen et al. | |
| 2010/0324578 | A1 * | 12/2010 | Bardy | A61M 37/0069 606/167 |
| 2010/0331868 | A1 | 12/2010 | Bardy | |
| 2011/0152611 | A1 | 6/2011 | Ducharme et al. | |
| 2013/0158587 | A1 * | 6/2013 | Euteneuer | A61B 17/8872 606/184 |
| 2013/0324977 | A1 | 12/2013 | Vanderpool | |
| 2014/0276928 | A1 | 9/2014 | Vanderpool et al. | |

FOREIGN PATENT DOCUMENTS

| | | |
|---|---|---|
| CN | 103908732 A | 7/2014 |
| CN | 104507526 A | 4/2015 |
| CN | 104797291 A | 7/2015 |
| GB | 632812 A | 12/1949 |
| JP | 2005534422 A | 11/2005 |
| JP | 2018-517497 A | 7/2018 |
| JP | 6654205 B2 | 2/2020 |
| WO | 2014150666 A1 | 9/2014 |

* cited by examiner

INTRODUCER WITH TISSUE POCKET OPTIMIZER

CROSS-REFERENCE TO RELATED APPLICATION

This application claims priority to Provisional Application No. 62/207,912, filed Aug. 21, 2015, which is herein incorporated by reference in its entirety.

TECHNICAL FIELD

The present disclosure relates to medical devices and methods for creating an pocket in a patient for an implantable medical device. More specifically, the disclosure relates to devices and methods for facilitating implantation of the implantable medical device under the patient's skin in a minimally-invasive and efficient manner.

BACKGROUND

Medical devices may be implanted subcutaneously under a patient's skin with minimal intervention and without the deeply positioning the device in the patient's body. Positioning of the medical device may be difficult due to high insertion forces necessary to manipulate the medical device and form a pocket for the device under the patient's skin. Improperly positioning functional aspects of the device may result in poor performance. This may include forming a pocket that is too large for the medical device, or forming a pocket having improper dimensions. Further, improper pocket formation may result in an implanted device being ejected from a patient as a result of the patient's normal movement. Thus, there is a need for an introducer device that allows for proper pocket formation and position of an implantable medical device within the pocket.

SUMMARY

In Example 1, an apparatus comprising a housing; and an inserter arranged at and extending from a distal portion of the housing, the inserter having at least a portion comprising a greater width than at least one other portion of the inserter.

In Example 2, the apparatus of Example 1, wherein the housing comprises a proximal portion including a proximal opening and distal portion including a distal opening, the proximal portion and the distal portion separating an intermediate portion sized to contain a medical device, and further comprising an ejection rod configured to pass through the proximal opening and eject the medical device from the housing through the distal opening of the housing.

In Example 3, the apparatus of Example 2, wherein the ejection rod comprises an outer circumference having at least one peak and at least one valley.

In Example 4, the apparatus of Example 3, wherein the proximal opening comprises surfaces complimentary to the at least one peak and the at least one valley of the ejection rod.

In Example 5, the apparatus of any of Examples 2, 3, or 4, further comprising a lock mechanism arranged at the proximal opening and configured to fix the ejection rod within the housing.

In Example 6, the apparatus of any of Examples 1-5, wherein the housing comprises a first surface and a second surface, and wherein the inserter is arranged at and extends from the housing at the second surface.

In Example 7, the apparatus of Example 6, wherein the housing further comprises a handle arranged at the proximal portion of the housing, and wherein the handle comprises a portion extending vertically beyond the first surface.

In Example 8, the apparatus of any of Examples 1-7, wherein the portion of the inserter comprising a greater width is arranged between a first and second other portion of the inserter having a lesser width.

In Example 9, the apparatus of any of Examples 1-8, wherein the inserter comprises a distal tip, and the portion of the inserter comprising a greater width tapers inwardly toward the other portion of the inserter toward the distal tip.

In Example 10, the apparatus of any of Examples 1-9, wherein the inserter comprises a first section and a second section and at least a portion comprising a greater width than at least one other portion of the inserter.

In Example 11, the apparatus of Example 10, wherein the first section and the second section are configured to separate from each other in response to an ejection rod ejecting the medical device from the housing.

In Example 12, the apparatus of Example 10, wherein the inserter comprises a distal tip, and the first section and the second section converge to form the distal tip.

In Example 13, the apparatus of Example 10, wherein the first section overlaps the second section, and the first section and the second section converge to form a distal tip of the inserter.

In Example 14, the apparatus of any of Examples 10-13, wherein the inserter comprises an opening between the first section and the second section, and the opening is sized to contain an implantable medical device.

In Example 15, the apparatus of Example 14, wherein the proximal opening comprises surfaces complimentary to the at least one peak and the at least one valley of the ejection rod.

In Example 16, an introducer apparatus for positioning an implantable medical device within a patient, the apparatus comprising a housing having a proximal portion including a proximal opening and distal portion including a distal opening, the proximal portion and the distal portion separating an intermediate portion sized to contain the implantable medical device; and an inserter arranged at and extending from the distal portion of the housing, the inserter having at least a portion comprising a greater width than at least one other portion of the inserter.

In Example 17, the apparatus of Example 16, wherein the inserter is configured to form a pocket within a patient, wherein the pocket is sized to surround the implantable medical device.

In Example 18, the apparatus of Example 16, wherein the inserter is configured to form an asymmetric pocket within a patient in response to the inserter having at least a portion comprising a greater width than the at least one other portion of the inserter.

In Example 19, the apparatus of Example 16, further comprising an ejection rod configured to pass through the proximal opening and eject the implantable medical device from the housing through the distal opening of the housing.

In Example 20, the apparatus of Example 19, wherein the ejection rod comprises an outer circumference having at least one peak and at least one valley.

In Example 21, the apparatus of Example 20, wherein the proximal opening comprises surfaces complimentary to the at least one peak and at least one valley of the ejection rod.

In Example 22, the apparatus of Example 16, wherein further comprising a handle arranged at the proximal portion of the housing, and wherein the handle comprises a portion extending vertically beyond the first surface.

In Example 23, the apparatus of Example 16, wherein the portion of the inserter comprising a greater width is arranged between a first and second other portion of the inserter having a lesser width.

In Example 24, the apparatus of Example 16, wherein the inserter comprises a distal tip, and the portion of the inserter comprising a greater width tapers inwardly toward the other portion of the inserter toward the distal tip.

In Example 25, a system comprising: an implantable medical device; an introducer comprising: a housing having a proximal portion including a proximal opening and distal portion including a distal opening, the proximal portion and the distal portion separating an intermediate portion sized to contain the implantable medical device; an ejection rod configured to pass through the proximal opening and eject the implantable medical device from the housing; and an inserter arranged at and extending from the distal portion of the housing, the inserter having at least a portion comprising a greater width than at least one other portion of the inserter, the inserter being configured to create a pocket for the implantable medical device within the patient and guide the implantable medical device into the pocket in response to the ejection rod ejecting the implantable medical device from the housing through the distal opening.

In Example 26, the apparatus of Example 25, wherein the inserter is configured to create the pocket having asymmetric dimensions.

In Example 27, the apparatus of Example 25, wherein the portion of the inserter comprising a greater width is arranged between a first and second other portion of the inserter having a lesser width.

In Example 28, the apparatus of Example 25, wherein the inserter comprises a first section and a second section, and wherein the first section and the second section are configured to separate from each other in response to the ejection rod ejecting the implantable medical device from the housing through the distal opening.

In Example 29, the apparatus of Example 28, wherein the inserter comprises a distal tip, and the first section and the second section converge to form a distal tip of the inserter.

In Example 30, the apparatus of Example 29, wherein the inserter comprises an opening between the first section and the second section, and the opening is sized to contain an implantable medical device.

In Example 31, a method of implanting an implantable medical device via an introducer, the method comprising: making an incision in a patient's skin; positioning the introducer within the incision, the introducer comprising a housing having a proximal portion including a proximal opening and distal portion including a distal opening, the proximal portion and the distal portion separating an intermediate portion sized to contain an implantable medical device, an ejection rod configured to pass through the proximal opening, and an inserter arranged at and extending from the distal portion of the housing and having at least a portion comprising a greater width than at least one other portion of the inserter; creating a pocket for the implantable medical device by inserting the inserter within the patient via the incision; and introducing the implantable medical device to the pocket within the patient by ejecting the implantable medical device via the ejection rod from the housing and through the distal opening.

In Example 32, the method of Example 31, wherein creating the pocket comprises rotating the inserter, and wherein the pocket comprises asymmetric dimensions.

In Example 33, the method of Example 32, wherein the housing further comprises a handle arranged at the proximal portion of the housing, and wherein the handle comprises a portion extending vertically beyond the first surface, and rotating the inserter rotates the portion of the handle extending vertically beyond the first surface away from the patient's skin.

In Example 34, the method of Example 31, wherein creating the pocket for the implantable medical device comprises forming the pocket having asymmetric dimensions including distal and proximal portions of having a smaller width than an intermediate portion of the pocket.

In Example 35, the method of Example 34, wherein the implantable medical device includes a first end, a second end, and an intermediate section, and introducing the implantable medical device to the pocket comprises positioning the first end and the second end of the implantable medical device within the portions of the pocket of a smaller width, and positing the intermediate section of the implantable medical device within the intermediate portion of the pocket.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1A:
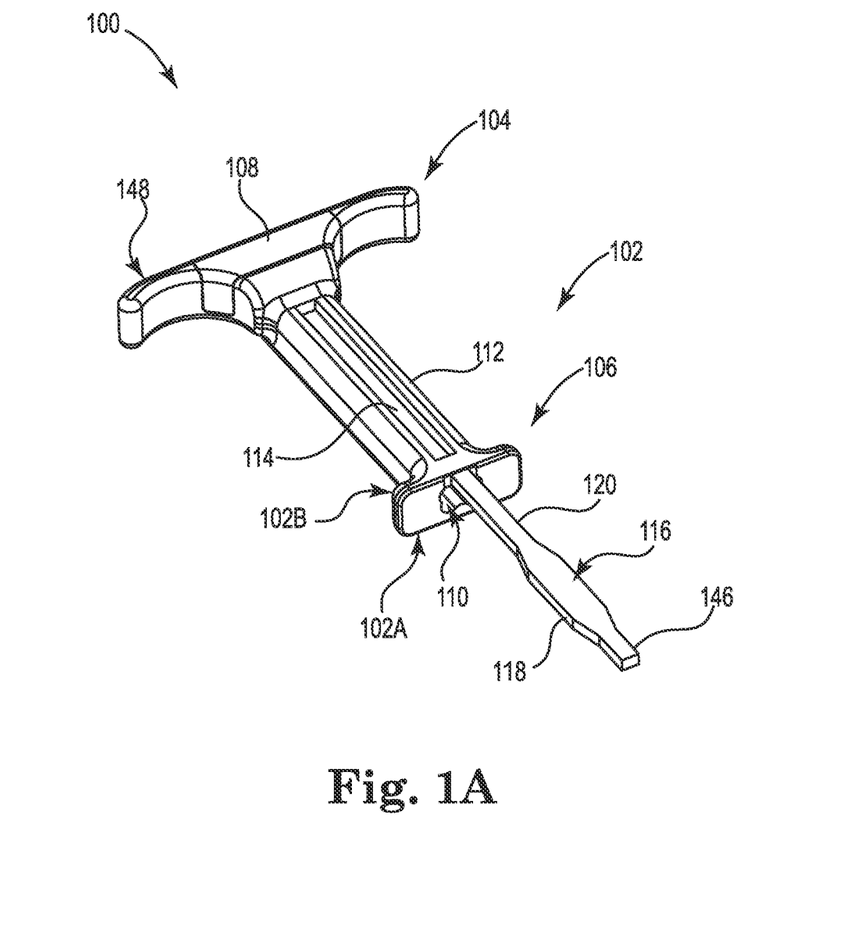
FIG. 1A shows a schematic illustration of an exemplary introducer apparatus for a medical device.

FIG. 1A shows a schematic illustration of an exemplary introducer apparatus 100 for a medical device. The introducer apparatus 100 includes a housing 102 having a proximal portion 104 and a distal portion 106. The proximal portion 104 may include a proximal opening 108 and the distal portion 106 may include a distal opening 110. The proximal portion 104 and the distal portion 106 are separated by an intermediate portion 112. As discussed in further detail below, the intermediate portion 112 may include an opening 114 that is sized and configured to contain an implantable medical device (not shown). For instance, the opening 114 in the intermediate portion 112 of the housing 102 may be formed or manufactured to accommodate medical devices of various sizes. The implantable medical device may be loaded into the housing 102 via either of the proximal opening 108 or the distal opening 110.

As also shown in FIG. 1A, the introducer apparatus 100 includes an inserter 116 that is arranged at and extends from the distal portion 106 of the housing 102. The inserter 116 may include at least one portion 118 that has a greater width than at least one other portion 120 of the inserter 116. As shown in FIG. 1A, the portion 118 that has a greater width is provided near distally to at least one other portion 120. The portion 118 that has a greater width may be formed of differing shapes so long as at least one portion of the inserter 116 has a greater width than the one other portion 120 of the inserter 116. The one other portion 120 may have a width that is substantially similar or approximately equal to the width of the implantable medical device. In addition, the portion 118 that has a greater width may have a width that is 1%, 5%, 10%, 15%, 20%, 25%, 30%, 35%, 40%, 45%, or 50% (or any percentage in between) greater than the width of the one other portion 120. In certain instances, the inserter 116 may include two portions 118, 146 that have a greater width than at least one other portion 120 of the inserter 116. The portion 146 may function as a tip of the inserter 116, which may facilitate movement of the inserter 116 through the tissue of a patient. The two portions 118, 146 of the inserter 116 may be of equal width, or may have differing widths.

The inserter 116 may be configured to create a pocket that is sized to surround the implantable medical device within the patient. In creating a pocket in a patient, an incision may be made in the patient's skin. The incision may be made by a separate device, such as a scalpel. After the incision is made, the inserter 116 may be manipulated within the patient through the incision. A user may then rotate the introducer apparatus 100. Rotation of the introducer apparatus 100 may create the pocket for an implantable medical device by forcing the tissue open. As a result of the inserter 116 having at least one portion 118 of a greater width than at least one other portion 120 of a inserter 116, the pocket for the implantable medical device may be formed as having asymmetric dimensions. The asymmetric dimensions of the pocket may be similar to the dimension of the inserter 116, while having a greater depth due to the rotation of the introducer apparatus 100. As shown in FIG. 1A, the inserter 116 includes a flat upper surface.

The housing 102 may include a first (or top) surface 102B and a second (or bottom) surface 102A. The introducer apparatus 100 also may include an inserter 116 arranged at and extending from the first (top) surface 102B. In other instances, the inserter 116 may extend from the second (bottom) surface 102A of the housing 102. In addition, the housing 102 may include a gripping portion 148 located at the proximal portion 104. The gripping portion 148 may provide depth to allow a user to grip and manipulate the introducer apparatus 100.

In certain instances, an implantable medical device (not shown) that is provided with the introducer apparatus 100 may be ejected from the intermediate portion 112 of the housing 102 by way of using a tool having a sufficient length that allows for a user to move the implantable medical device through the distal opening 110 of the housing 102, and that also passes through the proximal opening 108. In other instances, the introducer apparatus 100 may be provided with a specific tool, such as an ejection rod, as discussed with reference to FIG. 1B, to eject an implantable medical device from the housing 102.

Figure 1B:
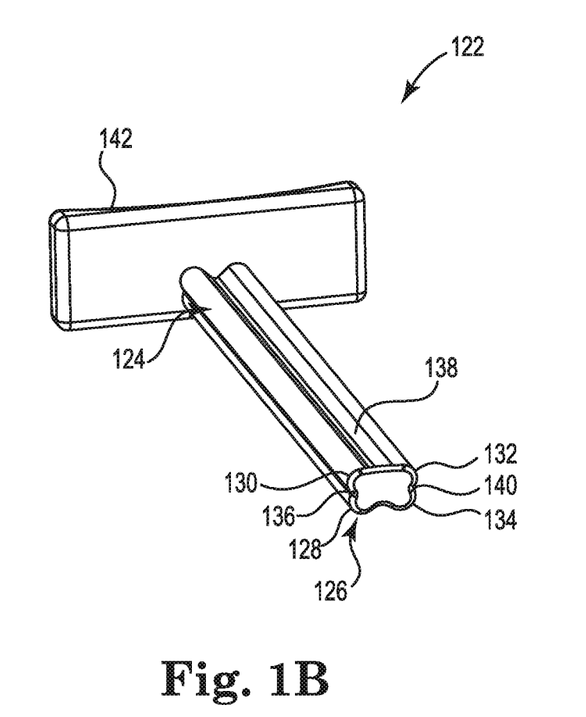
FIG. 1B shows a schematic illustration of an exemplary ejection rod that may be used in connection with the introducer apparatus, as shown in FIG. 1A.

FIG. 1B shows a schematic illustration of such an exemplary ejection rod 122 that may be used in connection with the introducer apparatus 100 shown in FIG. 1A. The ejection rod 122 may be provided with the introducer apparatus 100 to move/eject an implantable medical device from the housing 102. The ejection rod 122 includes a proximal portion 124 and a distal portion 126. In addition, the ejection rod 122 may be provided with the introducer apparatus 100, as shown in FIG. 1A, by passing the distal portion 126 through the proximal opening 108 of the introducer apparatus 100. The ejection rod 122 may include consistent geometry throughout its length, which may correspond to the length of the housing 102 of the introducer apparatus 100. As a result, the ejection rod 122 may pass through the proximal opening 108 of the introducer apparatus 100 such that an implantable medical device contained in the housing 102 may be ejected from opening 114 through the distal opening 110 of the housing 102. The proximal portion 124 of the ejection rod 122 may include a handle 142. A portion of the handle 142 may extend vertically beyond an outer surface of the introducer apparatus 100 when provided therewith. The handle 142 may provide an additional surface area for a user to grip the introducer apparatus 100. The handle may be useful in overcoming the force needed to implant an implantable medical device beneath the skin of a patient.

Figure 1C:
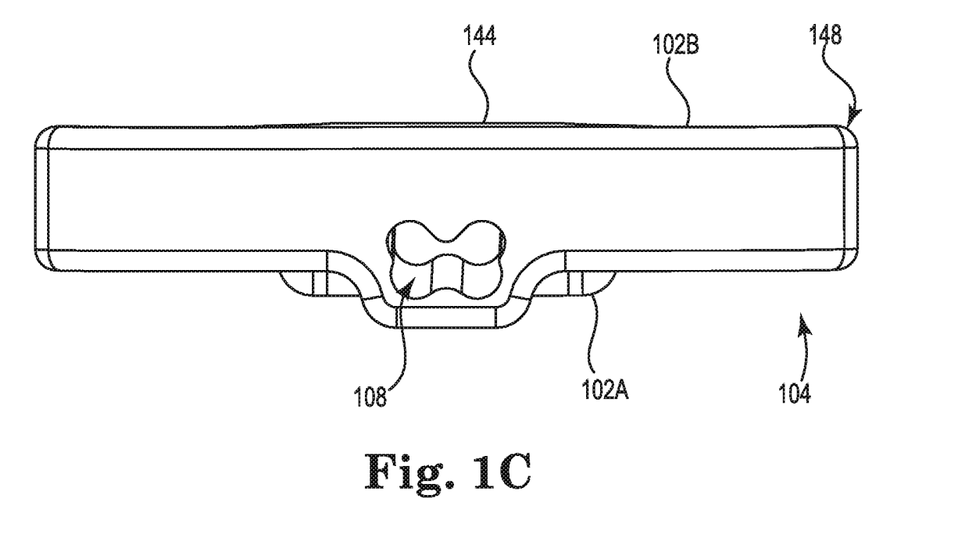
FIG. 1C shows a close-up schematic illustration the proximal portion and an exemplary lock mechanism that may be provided with the introducer apparatus, as shown in FIG. 1A.

FIG. 1C shows a close-up schematic illustration the proximal portion 104 and an exemplary lock mechanism 144 that may be provided with the introducer apparatus 100 shown in FIG. 1A. The lock mechanism 144 may be removeably secured to the proximal portion 104 of the introducer apparatus 100, and is configured to fix the ejection rod 122 within the housing 102. The lock mechanism 144 may include a surface that interacts with portions of the ejection rod 122 such that the ejection rod 122 is secured within the proximal opening 108 of the housing 102. As is also shown in FIG. 1C, the proximal opening 108 has a circumference that mirrors or corresponds to the peaks 128, 130, 132, 134 and valleys 136, 138, 140 of the ejection rod 122. As a result, the ejection rod 122 may be unique to the introducer apparatus 100. The proximal opening 108 may have a circumference that has other shapes, or a circumference that is symmetrical.

Figure 2:
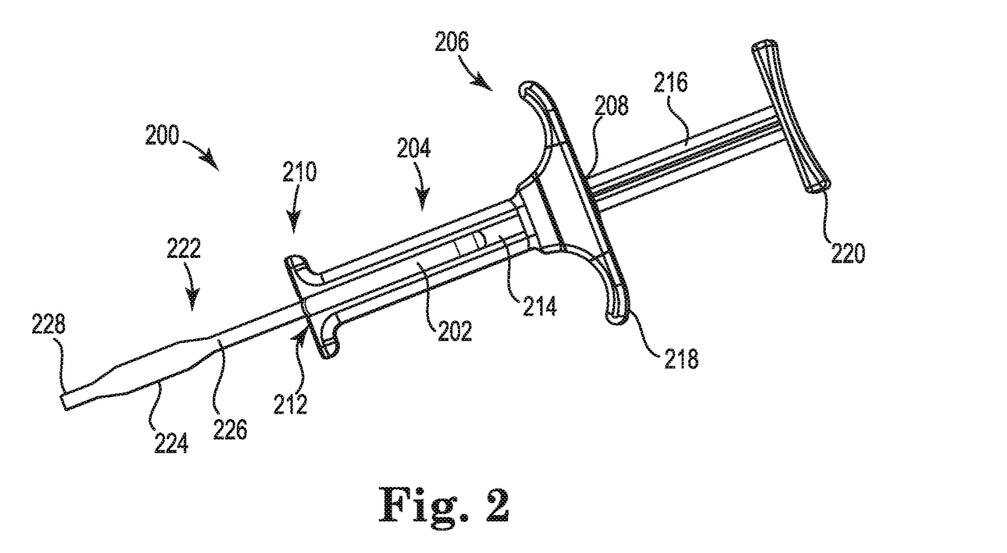
FIG. 2 shows a schematic illustration of an exemplary introducer apparatus and an implantable medical device.

FIG. 1C shows a close-up schematic illustration the proximal portion 104 and an exemplary lock mechanism 144 that may be provided with the introducer apparatus 100 shown in FIG. 1A. The lock mechanism 144 may be removeably secured to the proximal portion 104 of the introducer apparatus 100, and is configured to fix the ejection rod 122 within the housing 102. The lock mechanism 144 may include a surface that interacts with portions of the ejection rod 122 such that the ejection rod 122 is secured within the proximal opening 108 of the housing 102. As is also shown in FIG. 2C, the proximal opening 108 has a circumference that mirrors or corresponds to the peaks 128, 130, 132, 134 and valleys 136, 138, 140 of the ejection rod 122. As a result, the ejection rod 122 may be unique to the introducer apparatus 100. The proximal opening 108 may have a circumference that has other shapes, or a circumference that is symmetrical.

Also shown in FIG. 1C is the gripping portion 148 of the introducer apparatus 100. The gripping portion 148 is shown as offset from the second (or bottom) surface 102A and forming a part of the first (or top) surface 102B of the housing 102. When the introducer apparatus 100 is inserted into a patient, the second (or bottom) surface 102A may contact the skin of the patient. As result of the gripping portion 148 being offset from the second (or bottom) surface 102A, the user may manipulate the introducer apparatus 100 without obstruction from the patient's skin. More specifically, the introducer apparatus 100 may be inserted under the skin of a patient at a slight angle relative to the patient's skin or the introducer apparatus 100 may be inserted almost parallel to the patient's skin. As a result, the offset of the gripping portion 148 provides a user with additional space away from the patient's skin to manipulate the housing 102 and/or the ejection rod 122 when the introducer apparatus 100 is in use.

FIG. 2 shows a schematic illustration of an exemplary introducer apparatus 200 and an implantable medical device 202. The introducer apparatus 200 includes a housing 204 having a proximal portion 206 including a proximal opening 208, and distal portion 210 including a distal opening 212. An intermediate portion 214 separates the proximal portion 206 and the distal portion 210. The intermediate portion 214 is sized and configured to contain the implantable medical device 202.

The introducer apparatus 200 is also provided with an ejection rod 216 that is configured to pass through the proximal opening 208, and configured to eject the implantable medical device 202 from the housing 204. The ejection rod 216 and housing 204 may function similar to a plunger, such that the implantable medical device 202 is ejected from the housing 204 in response to a user applying force to the ejection rod 216 in a direction that is longitudinally along the body of the ejection rod 216 or substantially parallel with the length of the housing 204. In certain instances, one or both of the housing 204 and/or the ejection rod 216 may include handles 218, 220. The handles 218, 220 allow for addition grip for a user in manipulating the housing 204 and/or the ejection rod 216.

The introducer apparatus 200 also may include an inserter 222 arranged at and extending from the distal portion 210 of the housing 204. The inserter includes at least one portion 224 that has a greater width than other portions of the inserter 222. The portion 224 that has a greater width may be formed of differing shapes so long as at least one portion of the inserter 222 has a greater width than another portion of the inserter 222. As shown in FIG. 2, the inserter 222 may be provided with two portions 226, 228 that have a lesser width than the portion 224 that has a greater width. The portion 224 of the inserter 222 having a greater width is arranged between the two portions 226, 228 of the inserter 222 having a lesser width. In certain instances, one of the portions 228 of the inserter 222 may be considered a distal tip, which may taper distally inwardly. In addition, the other portions 226, 228 of the inserter 222 may have a width that is substantially similar or approximately equal to the width of the implantable medical device 202. Further, the portion 224 of the inserter 222 having a greater width may be have a width that is 1%, 5%, 10%, 15%, 20%, 25%, 30%, 35%, 40%, 45%, or 50% greater (or any percentage in between) than the width of the other portions 226, 228 of the inserter 222.

The inserter 222 may be configured to create a pocket sized to surround the implantable medical device 202 within the patient. The implantable medical device 202 may be guided into the pocket in response to the ejection rod 216 ejecting the implantable medical device from the housing 204 through the distal opening 212. In creating a pocket in a patient, an incision may be made in a patient's skin. The incision may be made by a separate device, or may be made by the inserter 222. After the incision is made, the inserter 222 may be manipulated within the patient through the incision, and the pocket for the implantable medical device 202 is then formed. The pocket for the implantable medical device 202 may be formed as having asymmetric dimensions due to the inserter having a portion 224 having a greater width than the other portions 226, 228 of the inserter 222.

In certain instances, the introducer apparatus 200 and the implantable medical device 202 may be provided as a system such that the implantable medical device 202 is loaded with the introducer apparatus 200. In addition to the introducer apparatus 200 and the implantable medical device 202, the system may also include a device for making an incision in a patient. This device for making the incision (not shown) may be any device having a sharp edge (such as scalpel). In addition, the incision may be made using a plunge cutter, or, for example, a vibratory plunge cutter as discussed in U.S. Provisional Patent No. 62/159,510, Titled "Vibratory Plunge Cutter," and herein incorporated by reference.

Figure 3A:
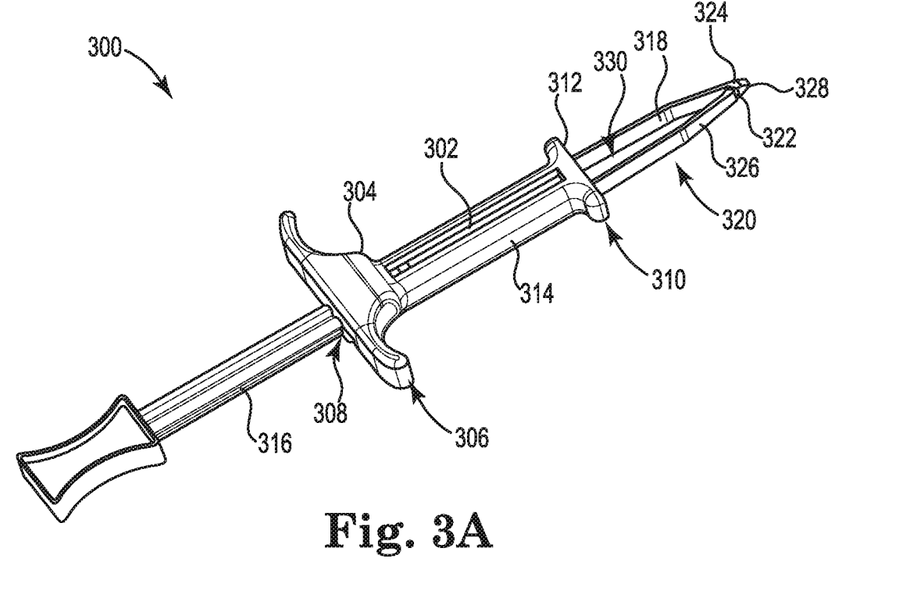
FIG. 3A shows a schematic illustration of another exemplary introducer apparatus and an implantable medical device.

FIG. 3A shows a schematic illustration of another exemplary introducer apparatus 300 and an implantable medical device 302. The introducer apparatus 300 includes a housing 304 having a proximal portion 306 including a proximal opening 308 and distal portion 310 including a distal opening 312, and an intermediate portion 314 sized to contain the implantable medical device 302 therebetween. The introducer apparatus 300 also includes an ejection rod 316 that is configured to pass through the proximal opening 308 and eject the implantable medical device 302 from the housing 304. Arranged at and extending from the distal portion 310 of the introducer apparatus 300 is an inserter 318.

As shown in FIG. 3A, the inserter 318 includes a portion 320 that has a greater width than another portion 322 of the inserter 318. In addition, each of the portion 320 and the another portion 322 of the inserter 318 include a first section 324 and a second section 326. The first section 324 and the second section 326 may converge to form a distal tip 328. The first section 324 may overlap the second section 326 in forming the distal tip 328 in certain instances. Further, the first section 324 and the second section 326 may form an opening 330 therebetween. Similar to the intermediate portion 314, the opening 330 is also sized to contain the implantable medical device 302. The first section 324 and the second section 326 are configured to separate from each other in response to the ejection rod 316 ejecting the implantable medical device 302 from the housing 304 through the distal opening 312. A user of the introducer apparatus 300 may apply a force to the ejection rod 316 to eject the implantable medical device 302 from the housing 304 through the distal opening 312 after the introducer apparatus 300 is positioned through an incision in the skin and within a patient.

Figure 3B:
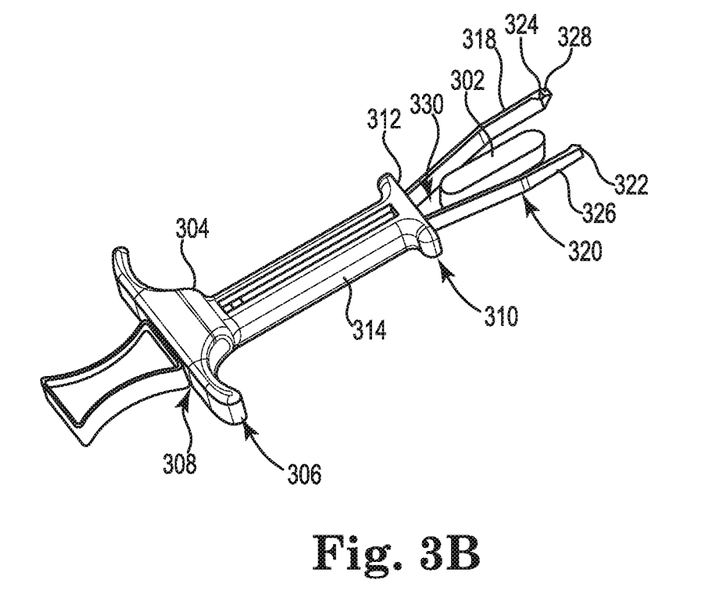
FIG. 3B shows a schematic illustration of the exemplary introducer apparatus and the medical device, as shown in FIG. 3A, with the implantable medical device positioned for implantation.

FIG. 3B shows a schematic illustration of the exemplary introducer apparatus 300 and the implantable medical device 302 shown in FIG. 3A with the medical device 302 positioned for implantation. As shown in FIG. 3B, the implantable medical device 302 has been positioned in the opening 330 between the first section 324 and the second section 326 in response to the ejection rod 316 ejecting the implantable medical device 302 from the housing 304 through the distal opening 312. The expansion of the first section 324 and the second section 326 may create a pocket within a patient by forcing apart tissue. The medical device 302 has a greater width than the portion 322. As a result, the ejection rod 316 will force the medical device 302 into the opening 330 until the medical device 302 contacts the portion 322 of the inserter 318 having a lesser width than the portion 320. This will force the first section 324 and the second section 326 to separate. In separating of the first section 324 and the second section 326, the first section 324 and the second section 326 will force apart tissue of a patient. This expansion of the first section 324 and the second section 326 creates a pocket within the patient. After expansion of the first section 324 and the second section 326 creates a pocket within the patient, the medical device 302 may be implanted within the pocket, and the introducer apparatus 300 may then be removed from the patient.

Figure 3C:
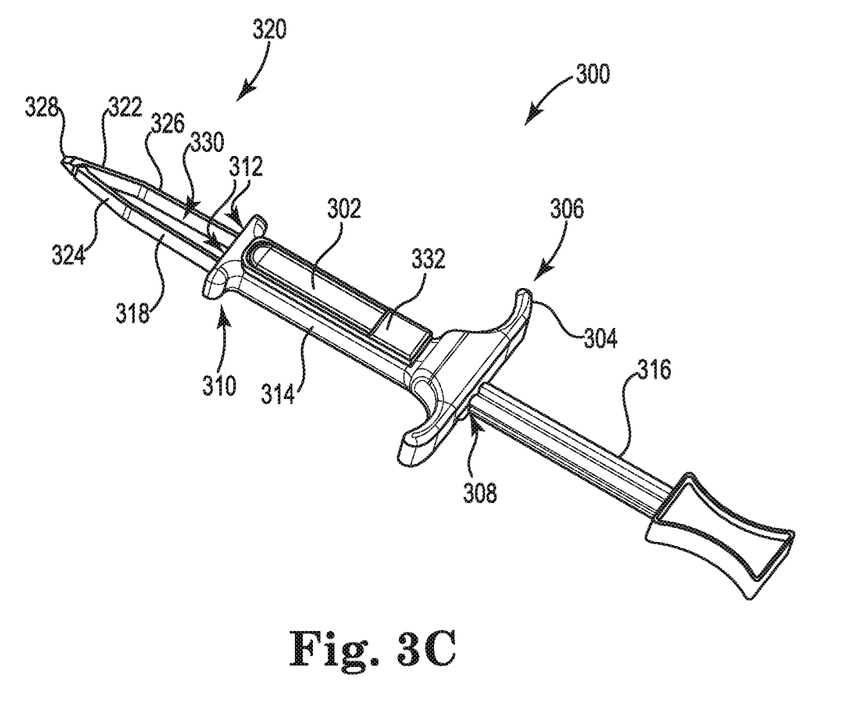
FIG. 3C shows a schematic illustration of the exemplary introducer apparatus and the medical device, as shown in FIGS. 3A-B, with a magazine to hold the medical device.

FIG. 3C shows a schematic illustration of the exemplary introducer apparatus 300 and the implantable medical device 302 shown in FIGS. 3A and 3B with a magazine 332 to hold the implantable medical device 302. The magazine 332 may be provided with the intermediate portion 314 of the introducer apparatus 300. The introducer apparatus 300. The magazine 332 may be formed as part of the intermediate portion 314, which is sized to contain the implantable medical device 302, and may house the implantable medical device 302, to allow for passage of the ejection rod 316 through both the proximal opening 308 and the distal opening 312 without contacting the implantable medical device 302. The magazine 332 positions the implantable medical device 302 to allow for contact with the ejection rod 316 after the ejection rod 316 is pulled toward the proximal opening 308, and pulled proximal to the magazine 332. Subsequently, the implantable medical device 302 may be positioned to contact the ejection rod 316 such that the ejection rod 316 ejects the implantable medical device 302 from the housing 304 through the distal opening 312, and positions the implantable medical device 302 in the opening 330 between the first section 324 and the second section 326.

Figure 4A:
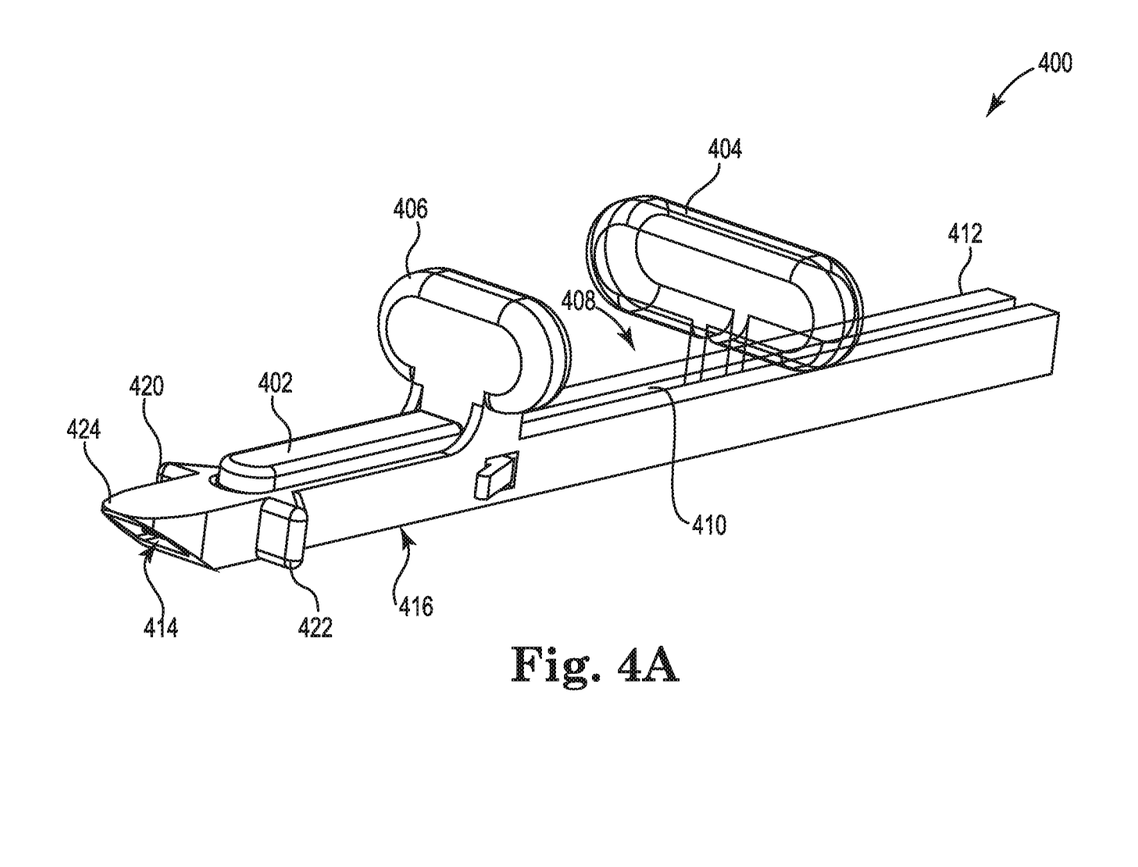
FIG. 4A shows a schematic illustration of another exemplary introducer apparatus and an implantable medical device.

FIG. 4A shows a schematic illustration of another exemplary introducer apparatus 400 and an implantable medical device 402. The introducer apparatus 400 includes a first handle 404 and a second handle 406. The first handle 404 is coupled to an ejection rod 418 (shown and discussed below with reference to FIG. 4D), and the second handle 406 is couple to a housing 408 of the introducer apparatus 400. The first handle 404 and the ejection rod slide along an opening 410 in the housing 408. As shown in FIG. 4A, both the first handle 404 and the second handle 406 extend vertically above a first (top) surface 412 of the introducer apparatus 400. In addition, the first handle 404 may slide along the opening 410 toward the second handle 406 in order to create a pocket under a patient's skin. The pocket may be created after positioning a distal opening 414 of the introducer apparatus 400 within an incision made in the patient's skin. The ejection rod 418 may extend out of the housing 408 via a distal opening 414, and in certain instances, the ejection rod 418 may form the incision made in the patient's skin.

Figure 4B:
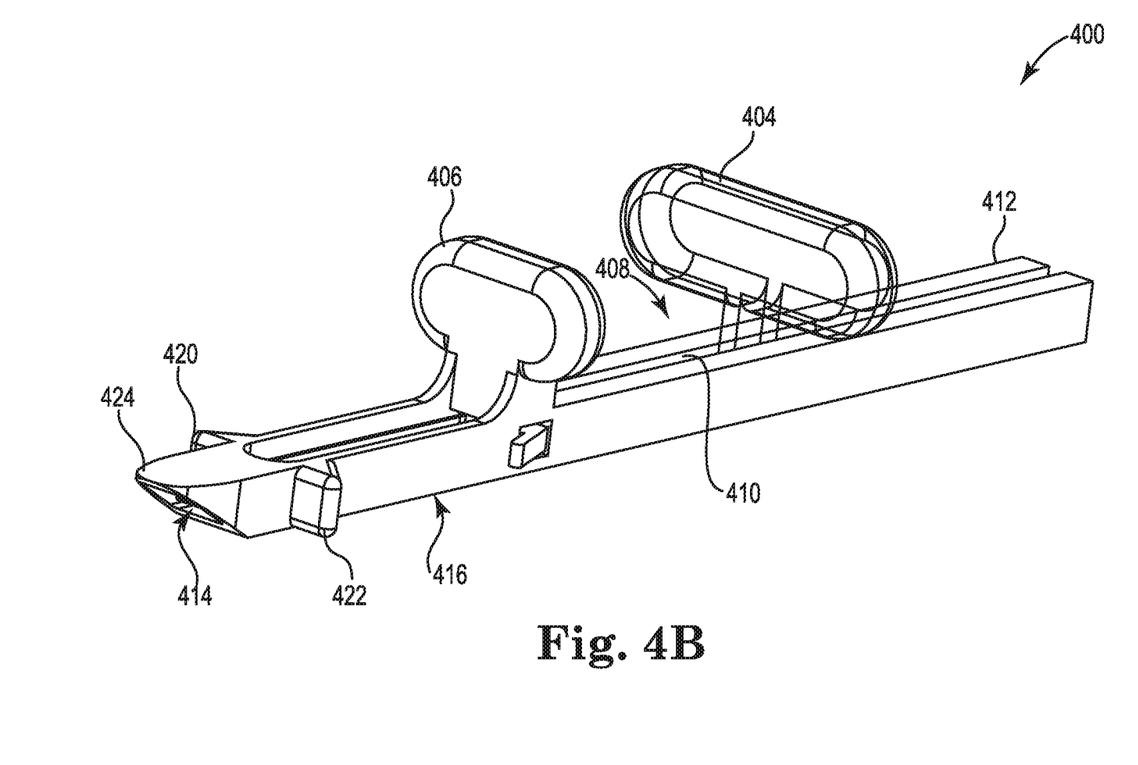
FIG. 4B shows a schematic illustration of the exemplary introducer apparatus, as shown in FIG. 4A, after a pocket is made under the skin by the introducer apparatus.

FIG. 4B shows a schematic illustration of the exemplary introducer apparatus 400, as shown in FIG. 4A, after the pocket is made under the skin by the introducer apparatus 400. After the pocket has been made, the first handle 404 is pulled back from the second handle 406. Before or after sliding back the first handle 404, the introducer apparatus 400 may be positioned within the incision. The implantable medical device 402 (not shown in FIG. 4B) drops into a space or opening 418 between the first (top) surface 412 of the introducer apparatus 400 and a second (bottom) surface 416. The first handle 404 may then again be slid along the opening 410 toward the second handle 406. This second movement of the first handle 404 ejects the implantable medical device 402 from the housing 408 through the distal opening 414 as is shown in FIG. 4C.

Figure 4C:
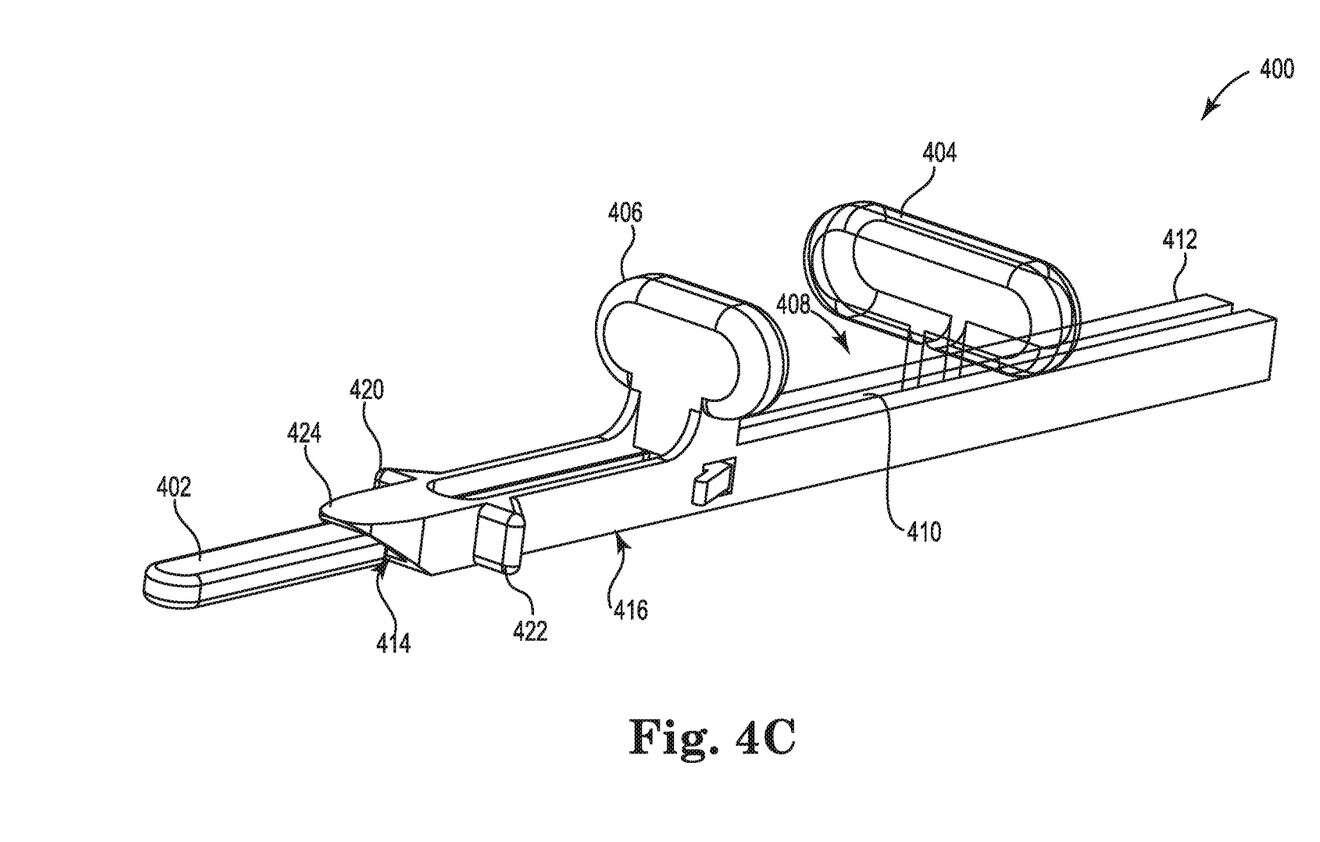
FIG. 4C shows a schematic illustration of the exemplary introducer apparatus, as shown in FIGS. 4A-B, and the implantable medical device with the implantable medical device positioned for implantation.

FIG. 4C shows a schematic illustration of the exemplary introducer apparatus 400, shown in FIGS. 4A-B, and the implantable medical device 402 with the implantable medical device 402 positioned for implantation. During implantation of the implantable medical device 402, the introducer apparatus 400 is positioned within an incision made in a patient's skin. More specifically, the introducer apparatus 400 may be positioned in a patient's skin until one or more stops 420, 422 touch the skin. As shown, the introducer apparatus 400 includes two stops 420, 422 that extend laterally away from the introducer apparatus 400. Further, the introducer apparatus 400 may also include a tip 424 that facilitates positioning of the introducer apparatus 400 under the patient's skin.

Figure 4D:
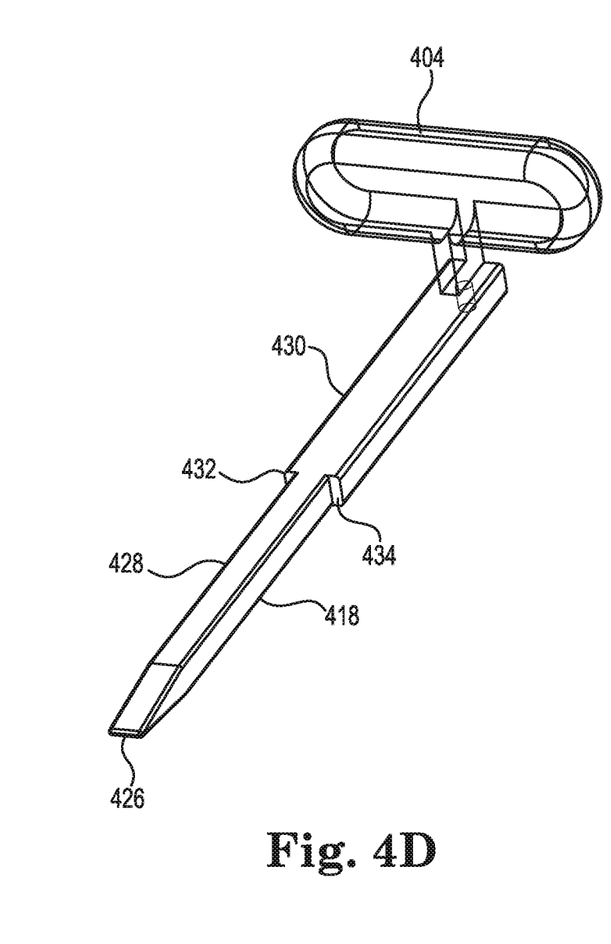
FIG. 4D shows a schematic illustration of an exemplary ejection rod used in connection with the exemplary introducer apparatus, as shown in FIGS. 4A-C.

FIG. 4D shows a schematic illustration of an exemplary ejection 418 rod used in connection with the exemplary introducer apparatus 400 shown in FIGS. 4A-C. The ejection rod 418 includes a tip 426, a first portion 428, and a second portion 430. The tip 426 of the ejection rod 418 may be configured to provide an incision in a patient. The tip 426 may also contact the implantable medical device 402, and transition the implantable medical device 402 along the opening 410 in the housing 408. In addition, the first portion 428 of the ejection rod 418 may have a greater width than the second portion 430 of the ejection rod 418. This includes a transition between the first portion 428 and the second portion 430 that may provide depth control of the implantable medical device 402 during implantation. For example, the transition between the first portion 428 and the second portion 430 may have edges 432, 434 that contact an internal portion of the distal opening 414 of the introducer apparatus 400.

Figure 5:
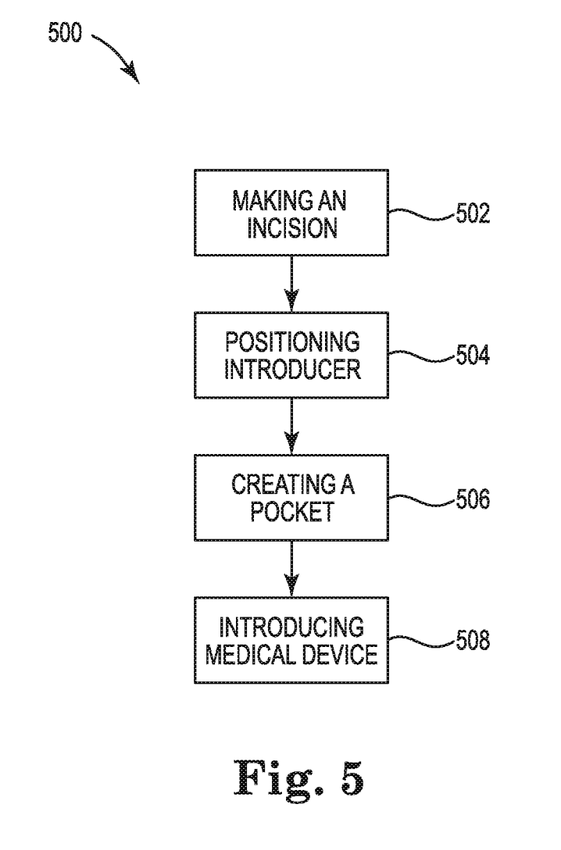
FIG. 5 is a flow diagram depicting an exemplary method of implanting an implantable medical device in accordance with the embodiments of the present invention.

FIG. 5 is a flow diagram 500 depicting an exemplary method of implanting an implantable medical device in accordance with embodiments of the present invention. As is shown at block 502, the method includes making an incision in a patient's skin. After the incision is made and as is shown at block 504, the method includes positioning the introducer within the incision. The introducer may include a housing having a proximal portion including a proximal opening and distal portion including a distal opening. Further, the introducer may also include an intermediate portion between the proximal portion and the distal portion, with the intermediate section being sized to contain an implantable medical device. Further, the introducer may include an ejection rod configured to pass through the proximal opening, and an inserter arranged at and extending from the distal portion of the housing and having at least a portion comprising a greater width than at least one other portion of the inserter. The introducer as used in the method is shown in further detail with reference to any of FIGS. 1-4.

In addition and as is shown at block 506, the method includes creating a pocket for the implantable medical device by inserting the inserter within the patient via the incision. In certain instances, creating the pocket for the implantable medical device may include rotating the inserter. Rotating the inserter and using an introducer with an inserter having a portion comprising a greater width than other portions permits for the creation of a pocket under the skin that has asymmetric dimensions. In certain instances, due to the implantable medical device often having symmetric dimensions, a pocket also having symmetric dimensions may squeeze or force the implantable medical device from the pocket after implantation. Thus, it may be beneficial to form a pocket having asymmetric dimensions to lessen the force along the body of the implantable medical device. The asymmetric dimensions may include a pocket that is less wide in the middle, a pocket that is less wide at its further end, or other such dimensions. The asymmetric dimensions allow for the implantable medical device to move slightly within the pocket after implantation in response to the patient's movement. Thus, the method may include forming the pocket having asymmetric dimensions that including distal and proximal portions having a smaller width than an intermediate portion of the pocket. The distal and proximal portions having smaller widths promotes electrical contact in the necessary positions, and also holds the implantable medical device in a central position. In certain instances, the housing of the introducer may include a handle arranged at the proximal portion of the housing. In addition, the handle may also include a portion that extends vertically beyond the first surface. In such instances, the method may include rotating the inserter that rotates the portion of the handle extending vertically beyond the first surface away from the patient's skin in the step of creating the pocket for the implantable medical device.

Further, as is shown at block 508, the method includes introducing the implantable medical device to the pocket within the patient by ejecting the implantable medical device via the ejection rod from the housing and through the distal opening. The implantable medical device used in the method described with reference to FIG. 5 may include a first end, a second end, and an intermediate section. One or more of the first end and the second end may include an electrode. To ensure proper functioning of the implantable medical device, the electrodes must make sufficient contact with the surrounding tissue. Thus, it may be beneficial in forming a pocket that has asymmetric dimensions, to ensure that the ends of the pocket that will contact the electrodes or ends of the implantable medical device when the implantable medical device is implanted have a lesser width than other portions of the pocket. As a result, the method may include, for the step of introducing the implantable medical, introducing the implantable medical device to the pocket by positioning the first end and the second end of the implantable medical device within the portions of the pocket of a smaller width, and positing the intermediate section of the implantable medical device within the intermediate portion of the pocket. This ensures contact between the electrodes of the implantable medical device and the tissue while maintaining the benefits of forming an asymmetric pocket.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An introducer apparatus for positioning an implantable medical device within a patient, the apparatus comprising:
a housing having a proximal portion including a proximal opening and distal portion including a distal opening, the proximal portion and the distal portion separating an intermediate portion sized to contain the implantable medical device; and
an inserter fixedly attached to and extending from a first surface or a second surface of the distal portion of the housing adjacent to and without extending into the distal opening, the inserter having at least a portion comprising a greater width between a first and second other portion of the inserter having a lesser width with the first other portion extending from the distal portion of the housing and the first and second other portion being approximately of equal width and the portion of greater width of the inserter includes a width less than a width of the distal portion of the housing, the inserter includes a flat external surface along at least the portion comprising the greater width, wherein the first other portion extends a first length measured from the housing to the portion of greater width, wherein the width of the first other portion is uniform along the entire first length.

2. The apparatus of claim 1, wherein the inserter is configured to form a pocket within a patient, wherein the pocket is sized to surround the implantable medical device.

3. The apparatus of claim 1, wherein the inserter is configured to form an asymmetric pocket within a patient.

4. The apparatus of claim 1, further comprising an ejection rod configured to pass through the proximal opening and eject the implantable medical device from the housing through the distal opening of the housing.

5. The apparatus of claim 4, wherein the ejection rod comprises an outer circumference having at least one peak and at least one valley.

6. The apparatus of claim 5, wherein the proximal opening comprises surfaces complementary to the at least one peak and the at least one valley of the ejection rod.

7. The apparatus of claim 1, further comprising a handle arranged at the proximal portion of the housing, and wherein the handle comprises a portion extending vertically beyond the housing.

8. The apparatus of claim 1, wherein the inserter comprises a distal tip, and the portion of the inserter comprising a greater width tapers inwardly toward the second other portion of the inserter toward the distal tip.

9. The apparatus of claim 1, wherein the flat external surface extends along an entire length of the inserter measured from the housing to a distal end of the inserter.

10. The apparatus of claim 1, wherein the second other portion extends a second length measured from a distal end of the inserter to the portion of greater width, wherein the width of the second other portion is uniform along the entire second length.

11. The apparatus of claim 1, wherein the second other portion extends a second length measured from a distal end of the inserter to the portion of greater width, wherein the second other portion has a flat surface along the entire second length.

12. The apparatus of claim 1, wherein the inserter has a uniform depth along an entire length of the inserter from housing to a distal end of the inserter.

13. A system comprising:
an implantable medical device;
an introducer comprising:
a housing having a proximal portion including a proximal opening and distal portion including a distal opening, the proximal portion and the distal portion separating an intermediate portion sized to contain the implantable medical device; and
an ejection rod configured to pass through the proximal opening and eject the implantable medical device from the housing; and
an inserter fixedly attached to and extending from the distal portion of the housing adjacent to and without extending into the distal opening, the inserter having at least a portion comprising a greater width arranged between a first and second other portion of the inserter having a lesser width with the first other portion extending from the distal portion of the housing and the first and second other portion being approximately of equal width and the portion of greater width of the inserter includes a width less than a width of the distal portion of the housing and a depth less than the greater width of the inserter, the inserter being configured to create a pocket for the implantable medical device within the patient and guide the implantable medical device into the pocket in response to the ejection rod ejecting the implantable medical device from the housing through the distal opening, the inserter includes a flat external surface along at least the portion comprising the greater width, wherein the first other portion extends a first length measured from the housing to the portion of greater width, wherein the width of the first other portion is uniform along the entire first length.

14. The system of claim 13, wherein the inserter is configured to create the pocket having asymmetric dimensions.

15. The system of claim 13, wherein the flat external surface extends along an entire length of the inserter.

16. The system of claim 13, wherein the second other portion extends a second length measured from a distal end of the inserter to the portion of greater width, wherein the width of the second other portion is uniform along the entire second length.

17. The system of claim 13, wherein the depth of the inserter is uniform along an entire length of the inserter.

18. A method of implanting an implantable medical device via an introducer, the method comprising:
making an incision in a patient's skin;
positioning the introducer within the incision, the introducer comprising a housing having a proximal portion including a proximal opening and distal portion including a distal opening, the proximal portion and the distal portion separating an intermediate portion sized to contain an implantable medical device, an ejection rod configured to pass through the proximal opening, and an inserter fixedly attached to and extending from the distal portion of the housing adjacent to and without extending into the distal opening, the inserter having at least a portion comprising a greater width between a first and second other portion of the inserter having a lesser width with the first other portion extending from the distal portion of the housing and the first and second other portion being approximately of equal width and the portion of greater width of the inserter includes a width that is less than a width of the distal portion of the housing, wherein the inserter includes a flat external surface along at least the portion comprising the greater width and wherein the first other portion extends a first length measured from the housing to the portion of greater width, wherein the width of the first other portion is uniform along the entire first length;
creating a pocket for the implantable medical device by inserting the inserter within the patient via the incision; and
introducing the implantable medical device to the pocket within the patient by ejecting the implantable medical device via the ejection rod from the housing and through the distal opening.

* * * * *